(12) United States Patent
Nehls

(10) Patent No.: US 8,932,358 B1
(45) Date of Patent: Jan. 13, 2015

(54) ANTERIOR INTERVERTEBRAL SPACER AND INTEGRATED PLATE ASSEMBLY AND METHODS OF USE

(71) Applicant: Daniel Nehls, Tacoma, WA (US)

(72) Inventor: Daniel Nehls, Tacoma, WA (US)

( * ) Notice: Subject to any disclaimer, the term of this patent is extended or adjusted under 35 U.S.C. 154(b) by 0 days.

(21) Appl. No.: 14/048,026

(22) Filed: Oct. 7, 2013

(51) Int. Cl.
 *A61F 2/44* (2006.01)
(52) U.S. Cl.
 CPC ........................................ *A61F 2/442* (2013.01)
 USPC ...................................................... 623/17.16
(58) Field of Classification Search
 USPC .............................. 623/17.11–17.16; 606/246
 See application file for complete search history.

(56) References Cited

U.S. PATENT DOCUMENTS

| | | | | |
|---|---|---|---|---|
| 5,534,031 | A * | 7/1996 | Matsuzaki et al. ......... | 623/17.11 |
| 5,683,394 | A * | 11/1997 | Rinner ........................ | 606/86 R |
| 6,235,059 | B1 * | 5/2001 | Benezech et al. .......... | 623/17.16 |
| 6,432,106 | B1 * | 8/2002 | Fraser ......................... | 623/17.11 |
| 6,547,823 | B2 * | 4/2003 | Scarborough et al. ..... | 623/17.16 |
| 6,855,168 | B2 * | 2/2005 | Crozet ........................ | 623/17.11 |
| 7,232,463 | B2 * | 6/2007 | Falahee ....................... | 623/17.11 |
| 7,850,731 | B2 * | 12/2010 | Brittan et al. .............. | 623/17.11 |
| 8,323,343 | B2 * | 12/2012 | Michelson .................. | 623/17.16 |
| 8,480,747 | B2 * | 7/2013 | Melkent et al. ............ | 623/17.16 |
| 2002/0120334 | A1 * | 8/2002 | Crozet ........................ | 623/17.11 |
| 2003/0028197 | A1 * | 2/2003 | Hanson et al. .............. | 606/99 |
| 2004/0034430 | A1 * | 2/2004 | Falahee ....................... | 623/17.16 |
| 2005/0015151 | A1 * | 1/2005 | Fortin et al. ................ | 623/17.13 |
| 2005/0085913 | A1 * | 4/2005 | Fraser et al. ................ | 623/17.11 |
| 2010/0070037 | A1 * | 3/2010 | Parry et al. ................. | 623/17.16 |
| 2012/0065688 | A1 * | 3/2012 | Nehls .......................... | 606/279 |
| 2012/0101580 | A1 * | 4/2012 | Lechmann et al. ........ | 623/17.16 |
| 2012/0197401 | A1 * | 8/2012 | Duncan et al. ............. | 623/17.16 |

* cited by examiner

*Primary Examiner* — Matthew Lawson
*Assistant Examiner* — Zade Coley
(74) *Attorney, Agent, or Firm* — Marc Baumgartner; Baumgartner Patent Law

(57) ABSTRACT

A precisely size matched intervertebral plate and spacer assembly for ensuring a tight fit within a disc space to promote spinal fusion, comprising: a "U-shaped" spacer configured to fit within the intervertebral space; and, a matching countersunk low profile "H-shaped" anterior plate joined perpendicularly to the spacer. The plate further comprises: a plurality of anchor members configured to attach to the junctions of the anterior cortex faces and the endplates; and, channels individually traversing through the anchor members for inserting screws into the vertebral bodies' cortical bone. The spacer comprises a hollow three-sided U-shaped member, comprising two opposing parallel side walls, and a perpendicular posterior wall, while lacking a superior, inferior, and anterior wall. The exterior walls of the plate and spacer are planar, while the interior walls of the spacer are curved to house a precisely fitting cylindrical graft, or other insert such as DBM, bone dust, bone paste, bone dowel with direct contact to the endplates to promote fusion.

18 Claims, 14 Drawing Sheets

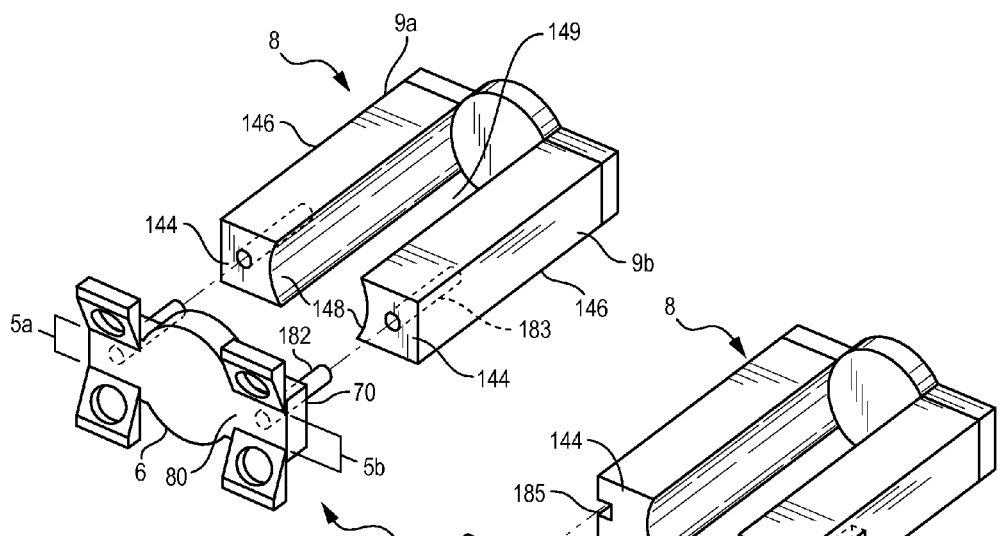
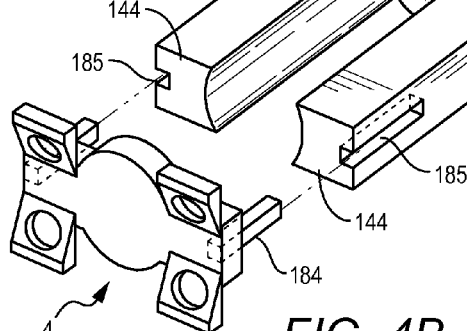
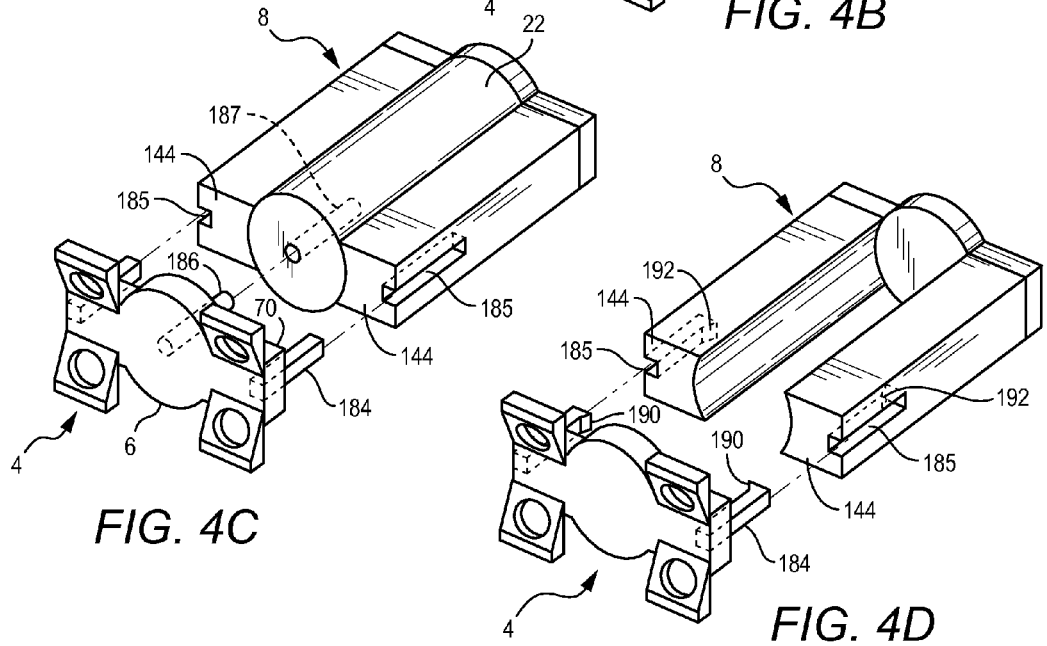
FIG. 4A  FIG. 4B  FIG. 4C  FIG. 4D

ANTERIOR INTERVERTEBRAL SPACER AND INTEGRATED PLATE ASSEMBLY AND METHODS OF USE

FIELD OF THE INVENTION

The embodiments herein relate to sets of intervertebral spacer and integrated plate assemblies and methods of use in spinal fixation procedures. More particularly, the teachings herein relate to improving current methods and systems directed to fusing one or more adjacent vertebral bodies within the cervical spine.

BACKGROUND

A human spine comprises 33 vertically aligned bone structures termed "vertebrae" or "vertebral bodies": 7 cervical, 12 thoracic, 5 lumbar, 5 sacral (fused into one bone, the sacrum), and 4 coccygeal (fused into one bone, the coccyx). Each vertebral body comprises a cylindrical structure composed of hard cortical bone on the outside and less dense cancellous bone on the inside, while the inferior and superior sides of each vertebral body are layered with end plates that are typically about 1 mm thick and comprise both bone and hyaline cartilage. Between each vertebral body is a flexible, connective tissue termed an "intervertebral disc" which secures one vertebral body to another and functions as a shock absorber. Degenerative discs are normally associated with the gradual breakdown of the structure of the disc and spinal canal due to age. Disk herniation is a rupture, often due to an acute injury, of fibrocartilagenous material (annulus fibrosis) that surrounds the intervertebral disk, and the release of the disk's center portion containing a gelatinous substance called the nucleus pulposus. Pressure from the vertebrae superior and inferior to the disc may cause the nucleus pulposus to be forced outward, placing pressure on a spinal nerve and causing considerable pain and damage to the nerve.

Spinal fixation is a surgical technique in which the damaged disc is removed between two vertebral bodies and replaced by a spinal implant to facilitate spine fusion between the bodies, while also stabilizing and strengthening the spine, and to mimic the cushioning effects of an endogenous disc. Disorders treated using spinal implants include degenerative disc disease, scoliosis, kyphosis, spondylolisthesis, and fracture.

Types of spine fusion or fixation surgery comprise: anterior cervical discectomy and fusion (ACDF) for the neck; and posterior and anterior lumbar spine fusion for the thoracic, lumbar, and sacral spine, wherein the terms "anterior" and "posterior" refer to the point of entry into the spine by the surgeon. Spine fusion surgeries can also be classified by "levels", meaning the number of intervertebral discs that are removed and fused together. For example, "one level" surgery refers to the removal of one disc and the fusion of two adjoining vertebral bodies, while a "two level" surgery refers to the removal of two consecutive discs and the fusion of the three vertebral bodies adjoining the discs.

Fusion implants generally comprise rods, plates, screws, interbody cages, and intervertebral spacers. The implants may be used with or without a bone autograft or allograft inserted in the disc space. Interbody cages are small hollow devices with perforated walls in which a bone autograft or allograft, or bone morphogenic protein (BMP) is inserted into the cage to promote bone fusion between the endplates of the inferior and superior vertebral bodies. Unfortunately, cages have been shown to have result in a high degree of subsidence, wherein subsidence of the cage was defined as a decrease in total vertical height of the two fused vertebral bodies as measured on the lateral cervical radiographs made 3 and 6 months postoperatively compared with the directly postoperative radiographs. (van Jonbergen HP, et al. "Anterior cervical interbody fusion with a titanium box cage: early radiological assessment of fusion and subsidence" *Spine J.* 2005 November-December; 5(6):645-9; discussion 649). In another study, the use of cage and plate construct in 2-level ACDF (Group B) resulted in a shorter fusion duration and a lower subsidence rate than that of cage alone (Group A), and wherein use of cage alone resulted in a subsidence rate of 35.71% (10/28) of group A as compared with 11.54% (3/26) of group B). (Oh J K, et al. "Stand-alone Cervical Cages Versus Anterior Cervical Plate in 2-Level Cervical Anterior Interbody Fusion Patients: Clinical Outcomes and Radiologic Changes", *J Spinal Disord Tech.* 2012 Feb. 23). Additionally, BMP has been labeled dangerous for use in ACDF by the US Food and Drug Administration because it may trigger swelling of neck tissues.

Spacers, which are biocompatible devices, are inserted into the disc space to promote spine fusion and stability, as well as to keep the spine from compressing the spinal nerves. The spacer is held in place by the pressure of the superior and inferior vertebral bodies, and can easily migrate posteriorly into the spinal canal and cause compression and pain from impingement of the spinal cord or nerves. This approach also has disadvantages in that attachment to the vertebral endplates is not as strong as attachment to the hard anterior cortex of the vertebrae, as seen in flat plates.

Flat plates, such as an anterior cervical plate for use in ACDF, are affixed to the anterior cortex of the spine by screws placed into superior and inferior vertebral bodies (see FIG. 1), and the plate may be used with or without a intervertebral spacer, bone graft, and/or cage. When used with a graft, the anterior cervical plate is generally effective in preventing interbody graft dislodgement toward the esophagus (which causes ostoperative dysphagia), and it also enhances spinal fusion by providing fixation between the vertebral bodies. But, this method can be disadvantageous as these plates are generally not low-profile, resulting in post-operative dysphagia, and recurrent laryngeal nerve palsy (Fountas K N, et al. Anterior cervical discectomy and fusion associated complications. *Spine (Phila Pa 1976).* 2007 Oct. 1; 32(21):2310-7). ACDF plates also tend to be long and may encroach upon the space of an adjacent disc space or vertebral body, which may lead to disc degeneration. And when an ACDF plate is used with a spacer, the surgeon first implants the spacer into the intervertebral space, and then tries to mix and match a plate that will fit the size of the spacer. This is a tedious and cumbersome procedure to perform during surgery.

Accordingly, there is a need in the art for improved spinal plates and spacer assemblies that have one or more of the following characteristics: a lower profile plate to reduce the risk for post-operative dysphagia; that promotes implant stability by preventing slippage and/or rotation of the bone graft and/or spacer within the interbody space; that prevents the migration of a interbody spacer and graft into the spinal canal; and/or that provides a tight fit between the spacer and graft and the adjoining superior and inferior endplates so as to promote spine fusion.

SUMMARY OF THE INVENTION

The vertebral plate and spacer assemblies of the present invention comprise a spacer that is size paired with an anterior plate, such that the once the surgeon selects the appropriate spacer size to fit tightly within a cylindrical hole based upon the diameter of the intervertebral drilling instruments (e.g. reamer and milling guide), then the plate is also selected (versus the surgeon trying to mix and match plates during surgery). Since the spacer also matches the diameter of the drilling instruments, it precisely fits within the intervertebral space to form a tight fit against the superior and inferior endplates to promote spine stability and fusion.

In one embodiment, the anterior plate is fixed on the anterior surface of the patient's cervical spine for a "one level" Anterior Cervical Discectomy and Fusion (ACDF). In another embodiment, the plate-spacer assembly is used in an Anterior Lumbar Interbody Fusion (ALIF) in which the disc is accessed from and removed via an anterior abdominal incision.

In all embodiments, the vertebral spacer-plate assembly is adapted to be permanently implanted partially or almost completely within an intervertebral space between superior and inferior vertebral bodies having anterior cortex faces and vertebral endplates. The assemblies comprise: 1) a "U-shaped" spacer configured to fit within the intervertebral space; and, 2) a countersunk "H-shaped" anterior plate joined perpendicularly to the open end of the spacer, and configured to be slightly protruding from the intervertebral space after being implanted (i.e. a low profile plate).

The assembly further comprises: 1) a plurality of anchor members coupled to the anterior surface of the H-shaped anterior plate wherein anchor members are configured to abut against the anterior cortex faces of the superior and inferior vertebral bodies when the vertebral plate assembly is implanted; and, 2) channels individually traversing through the plurality of anchor members and adapted to receive means for securing the vertebral plate assembly to the superior and inferior vertebral bodies, wherein the channels traverse through the corners or junctions of the anterior cortex faces and vertebral endplates of the superior and inferior vertebral bodies and into the vertebral bodies' cortical bone when the plate-spacer assembly is implanted.

U-Shaped Spacer

The "U-shaped" spacer is an essentially a three-sided rectangular or U-shaped member, comprising two opposing parallel side walls, and a posterior wall perpendicular to the side walls, and permanently affixed thereto. The posterior wall may comprise a separate posterior plate that permanently attaches to the posterior end of the spacer. The spacer also comprises an open end on the anterior side that is covered by the anterior plate after the spacer is implanted into the intervertebral space. The plate is also pre-sized, or manufactured, to fit the spacer with a tight seal; and the surgeon selects a plate-spacer assembly based on the size of the spacer (e.g. diameter and length) fitting tightly within the hole drilled into the intervertebral space/disc. The external surfaces of the spacer-plate assembly can comprise planar surfaces, or substantially so.

The spacer preferably is hollow. In one embodiment the spacer is hollow with the two parallel sides of the spacer creating an internal cylindrical cavity or chamber due to the internal surface of the side walls possessing a cylindrically curved surface. The external surfaces of the side walls remain planar.

The spacer may further comprise an inferior and superior side wall (i.e. top and bottom); or they may lack this. The absence of the walls may permit spine fusion between the endplates of the inferior and superior vertebral bodies and through the spacer chamber, especially in the presence of a bone graft residing within the spacer.

In one embodiment, the spacer chamber may be filled with any suitable insert such as bone paste, bone dowel, demineralized bone matrix (DBM), bone dust, or a graft to further promote spine fusion, such as a cylindrically shaped bone dowel or milled bone. The size of the graft or insert is matched with the size of the spacer's internal chamber to create a tight fit that does not permit rotation or shifting of the graft or insert within the spacer. The graft or insert may be slid into place within the spacer after the spacer is implanted during surgery, or it may be inserted pre-op. In this embodiment, spine fusion is optimized: because the spacer lacks an inferior and superior side wall such that the graft is in direct contact with the inferior and superior endplates; and, because the graft is stable within the spacer to promote protein bonding and adhesion to the endplates.

The U-shaped interbody spacer may further comprise a posterior side wall that rests against a "stop", or shelf created by the surgeon drilling into endplates of the inferior and superior vertebral bodies near the posterior face of the bodies. The top and bottom edges of the external surface of the spacer posterior wall/plate rest against the anterior facing shelf to prevent slippage of the spacer posteriorly into the spinal canal.

The spacer posterior wall may further comprise multiple shapes, such as cylindrical, rectangular, square, and cross (see FIGS. 5A-5D). Different shapes can allow a medical provider to have different or larger viewing areas into the intervertebral space. For example, FIG. 5D allows more visibility into the intervertebral space compared to FIG. 5C.

H-Shaped Anterior Plate

Preferred anterior plates of the present invention comprise an essentially planar "H-shaped" vertebral plate comprising: 1) a "middle" member residing in the center of the plate (e.g. middle of the "H"); and, 2) two "outer" members extending from the opposing sides of the middle member. A multitude of suitable or similar shapes can alternatively be used. In one embodiment, the middle member is circular or oval; and, the outer members are rectangular or square. The middle (e.g. circular) member is size matched to fit the hole created by the surgeon when drilling into the disc during the discectomy; and, to fit the chamber (e.g. cylindrical) on the anterior end of the size matched U-shaped spacer. The rectangular members are also partially or nearly completely countersunk into a space created by the surgeon on the anterior surface of the intervertebral space. Therefore, only the anchor members and a small extension of the anterior surface of the spacer-plate assembly reside outside of the intervertebral space (i.e. the anterior side/surface of the rectangular shaped member and circular member reside primarily aligned with the anterior face of the intervertebral space). The low profile of the plate thus significantly reduces the risk of the patient developing dysphagia and other medical complications as a result of the implant protruding anteriorly from the intervertebral space.

The anterior plate further comprises a plurality of anchor members coupled to the anterior surface of the H-shaped anterior plate wherein the anchor members are configured to abut against the anterior cortex faces of the superior and inferior vertebral bodies when the vertebral plate assembly is implanted.

Each anchor member may comprise a variety of shapes, circular, square, rectangular, etc. designed to minimize the profile of the anchor member anteriorly. The anchor members further comprise a fastener channel individually traversing through each anchor member and adapted to receive means (e.g. screws) for securing the spacer-plate assembly to the superior and inferior vertebral bodies. The channels also traverse through the corners or junctions made by a vertebral body's anterior cortex face and end plate.

In one embodiment, there are four square anchor members, one each positioned on each of the four corner ends of the outer member (one per each inferior and superior end of the H-shaped member), wherein each member has a tapered anterior profile so that it lays flush with its point of contact with the anterior face of the anterior plate. Each anchor member further comprises a fastener channel consisting of a hole within the center of an anchor member for threading a screw, or other fastener device, to secure the plate to the anterior cortex face of a superior or inferior vertebral body. The hole may thus possess helical threads to match and guide the screws. The anchor member is affixed to the junction created by the anterior cortex face and the intervertebral endplates of the vertebral bodies. The placement of the anchor members also permits the screws to be angled as compared to prior art anterior plates, i.e. horizontal aligned or substantially so, and resulting in the fastener devices being securely fixed into the cortical bone of the superior and inferior vertebral bodies versus the soft endplate.

The posterior surface of the anterior plate may further comprise various complementary means of fixing the plate to the spacer, such as male-female connectors wherein the male connector extends perpendicularly from the posterior plate of the plate to join the female connector on the anterior face of the spacer (see FIGS. 4A-4D). In one embodiment, the male connectors are rectangular or cylindrical and sized to tightly slide into matching cavities within the anterior face of the side walls of the spacer. The center of the posterior face of the plate may also comprise a cylindrical or square pin that fits within a matching hole within the graft (e.g. bone dowel) residing within the spacer.

The anterior plate in the assemblies may further comprise a hinged anterior plate as disclosed in U.S. Patent Application 20120065688 by Nehls, which is hereby expressly incorporated by reference herein in its entirety, and comprising a hinge member running laterally down the middle of the plate to allow the plate to flex, or angle towards the vertebral column at a limited angle so as to apply compressive loads to the spacer and thus enhance fusion of the superior and inferior vertebral bodies. The posterior surface of the hinge plate preferably comprises a circular member with a diameter matching the diameter of the hollow cylindrical cavity within the spacer. Therefore, when the posterior surface of the hinge plate is joined to the anterior surface of the spacer, it forms a tight seal to prevent rotation or shifting of the graft within the spacer. The hinge plate may further comprise male/female connectors to further secure the plate to the spacer comprising male members (e.g. cylindrical, rectangular, etc.) extending perpendicular and posteriorly from the posterior face of the hinge plate into female cavities residing on the anterior surface of the spacer. The male members can reside on the rectangular members of the plate and/or in the circular member. In the latter case, the female cavity resides in the center of the graft (e.g. bone dowel).

In another embodiment of the plate-spacer assembly, the anterior plate may lack anchor members positioned on the plate. Two or more fastener channels are instead located within and traverse through the middle (e.g. circular) member of the plate with one or more fastener devices (e.g. screws) angled into the superior and inferior vertebral bodies. This embodiment can be readily interchangeable with other anterior plates disclosed herein.

Method of Implantation

Further embodiments of the present invention comprise the method of use of the spacer-plate assembly, wherein the steps comprise: a) providing a U-shaped spacer; b) an H-shaped plate that size matches the spacer as disclosed supra; c) performing a discectomy, and then creating a substantially rectangular space within the anterior face of an intervertebral space sufficient to countersink the plate; and surgically creating a (e.g. cylindrical) hole extending posteriorly from and perpendicular to the anterior face and centered within the rectangular space; d) inserting the U-shaped spacer into the hole with the open anterior end facing the anterior end of the intervertebral space; e) affixing the H-shape plate by inserting the posterior face of the middle (e.g. circular) member into the open anterior end of the spacer while concurrently inserting the posterior face of the outer (e.g. rectangular) members into the rectangular space created in the intervertebral space. This is done until the anterior face of the plate is substantially aligned with, or extending slightly anteriorly from, the anterior face of the intervertebral space. At this point the plurality of anchor members abut against the anterior cortex faces, and the channels traverse through the junctions (i.e. corners) of the anterior cortex faces and vertebral endplates of the superior and inferior vertebral bodies and into the vertebral bodies' cortical bone. At this point, the method further comprises inserting fastener means for securing the plate and spacer assembly, such as screws threaded through the channels at the junctions of the vertebral bodies and into the cortical bone.

The countersinking of the H-shaped plate and its precise size match with the spacer enables the plate to remain in place within the intervertebral space as the surgeon drills holes into the anterior cortex through the plate's anchor members, and then inserts screws into the holes and through the channels.

In another embodiment of the plate-spacer assembly that lacks anchor members, the method of implantation is similar, with the exception that the channels traverse through the middle member of the spacer.

BRIEF DESCRIPTION OF THE DRAWINGS

It will be appreciated that the drawings are not necessarily to scale, with emphasis instead being placed on illustrating the various aspects and features of embodiments of the invention, in which:

FIGS. 4A-4D are exploded perspective views illustrating different embodiments of the male-female connectors between the plate and spacer.

FIG. 4A is a perspective view illustrating two cylindrical male connectors; and FIG. 4B illustrates two rectangular male connectors, all of which are extending from the posterior surface of the anterior plate into female cavities on the spacer's external surface of the side walls.

FIG. 4C is a perspective view illustrating an additional male-female connector extending from the center of the posterior surface of the anterior plate and into a female cavity within the center of the graft (e.g. bone dowel) seated within the spacer. FIG. 4D is a perspective view showing male locking pins and complementary female recesses.

DETAILED DESCRIPTION OF THE ILLUSTRATED EMBODIMENTS

Embodiments of the present invention are described below with reference to the above described Figures. It is, however, expressly noted that the present invention is not limited to the embodiments depicted in the Figures, but rather the intention is that modifications that are apparent to the person skilled in the art and equivalents thereof are also included.

Intervertebral Plate-Spacer Assembly

Figure 1:
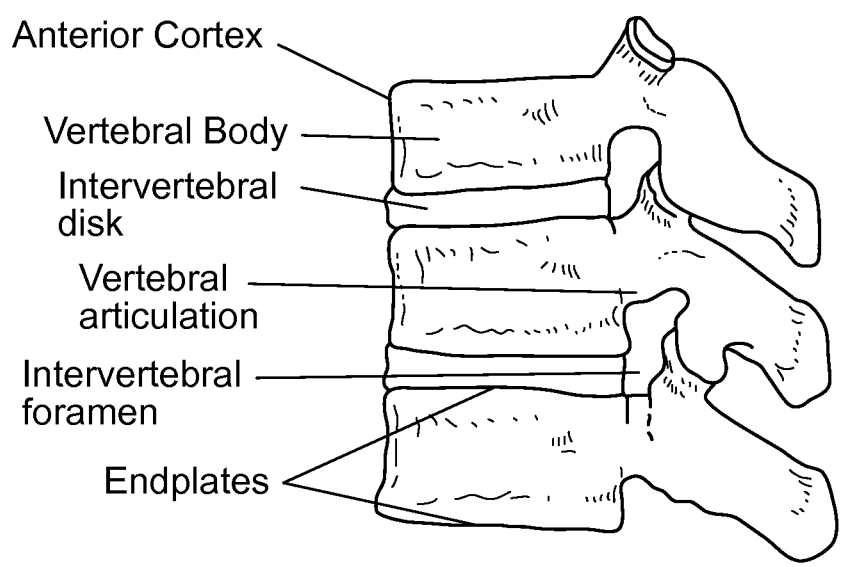
FIG. 1 is a prior art side view of the spine illustrating the anatomy of intervertebral discs, and vertebral bodies with endplates and anterior cortex faces.

The following disclosure is for one embodiment exemplified in the figures comprising a plate with a circular middle member and rectangular outer members. And unless stated otherwise, the term "intervertebral plate and spacer assembly" 2 as used herein generally relates to spinal implants comprising an H-shaped anterior plate, whether hinged or non-hinged, that is size matched to a hollow U-shaped cylindrical spacer, wherein the spacer may or may not comprise a superior and inferior wall. All Figures herein demonstrate an embodiment of the assembly comprising a spacer that lacks a superior and inferior wall such that the superior and inferior surfaces of the side arms of the spacer make direct contact with the superior and inferior endplates (see FIG. 1).

Figure 2A:
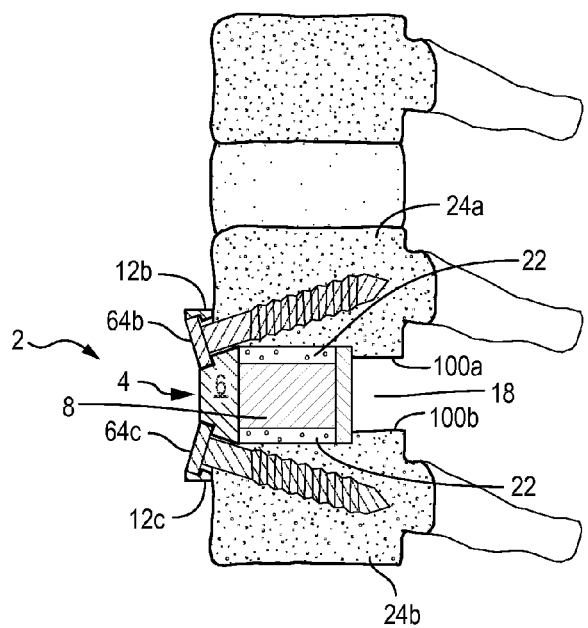
FIG. 2A is a side view illustrating a plate-spacer assembly implanted within spine.
Figure 2B:
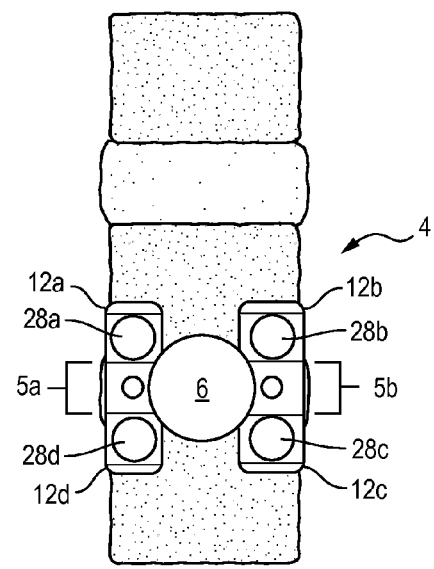
FIG. 2B is an anterior view of a plate-spacer assembly illustrating the H-shaped plate countersunk within the intervertebral space, and four anchor members affixing the plate to the junction of the anterior cortex face and endplates of the superior and inferior vertebral bodies.

In particular, FIGS. 2A, 2B, illustrate one embodiment comprising an Anterior Cervical Discectomy and Fusion (ACDF) assembly in vivo and the FIGS. 9A-9I illustrate the method of implanting the assembly into the cervical spine. It is also noted that FIGS. 2A, and 9A, 9C-9D, and 9F-9I are cross sectional views of the plate-spacer assembly taken along projection line 2A,8-2A,8 of FIG. 3A. This projection line represents the cross sectional view of the assembly through the right sided anchor members 12b,c of plate 4 and the arm 9b of the spacer 8. And FIGS. 3A, 3B, 4A-4D, 5A-5D, and 7A illustrate the assembly 2 ex vivo, or prior to implantation.

As shown in FIGS. 2A, 2B, 3A, 3B, and 4A-4D the item numbers representing the primary components of one embodiment of the assembly are as listed: 2 indicates the entire assembly on one embodiment comprising the H-shaped anterior plate 4, comprising a middle (e.g. circular) member 6 surrounded by two outer or lateral (e.g. rectangular) members 5a,b and anchor members 12a-d, and the U-shaped spacer 8. (In an alternative embodiment shown in FIGS. 7A and 7B, the anterior plate may comprise a hinge plate 10, as disclosed in U.S. Patent Application 20120065688 to Daniel G. Nehls.) FIG. 2A further provides a cross-sectional view of the assembly 2 implanted between superior and inferior vertebral bodies 24a,b and into the intervertebral space 18, and using fastener devices with fastener heads (only 64b,c shown) residing in the anchor members 12a-d (only 12b,c shown in a cross sectional view) while the fastener bodies 60a,b traverse through the fastener channels 28a-d (see FIG. 2B).

Figure 3A:
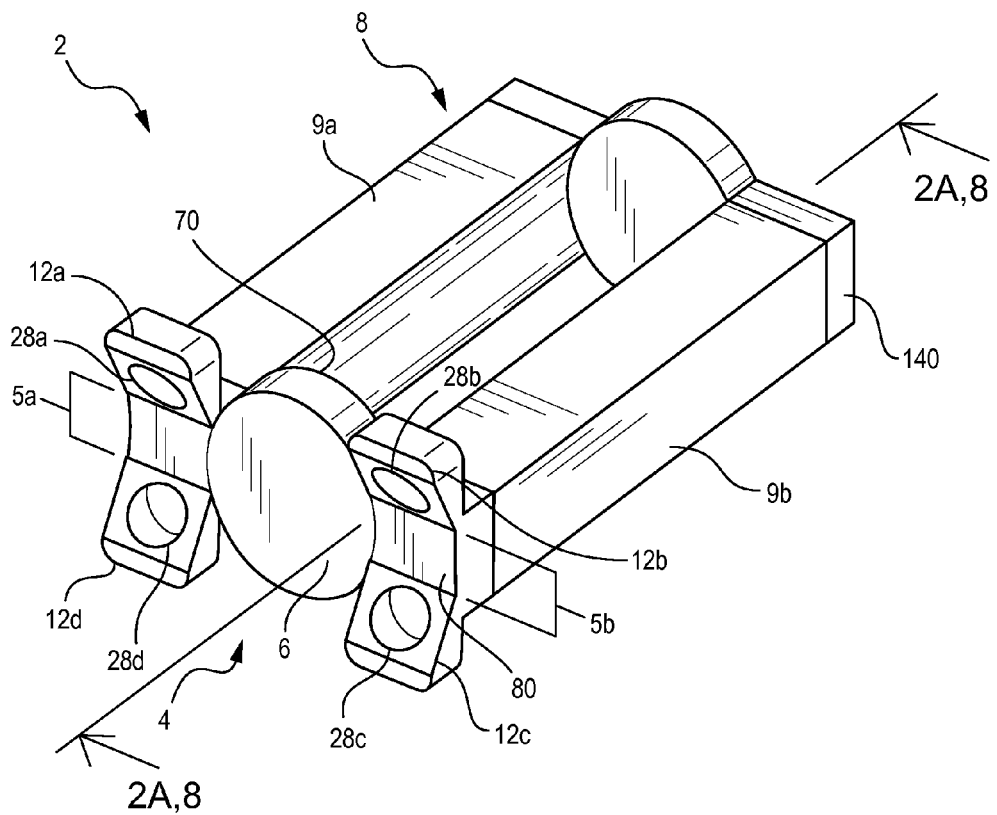
FIG. 3A is an elevated perspective view of a vertebral plate-spacer assembly.
Figure 3B:
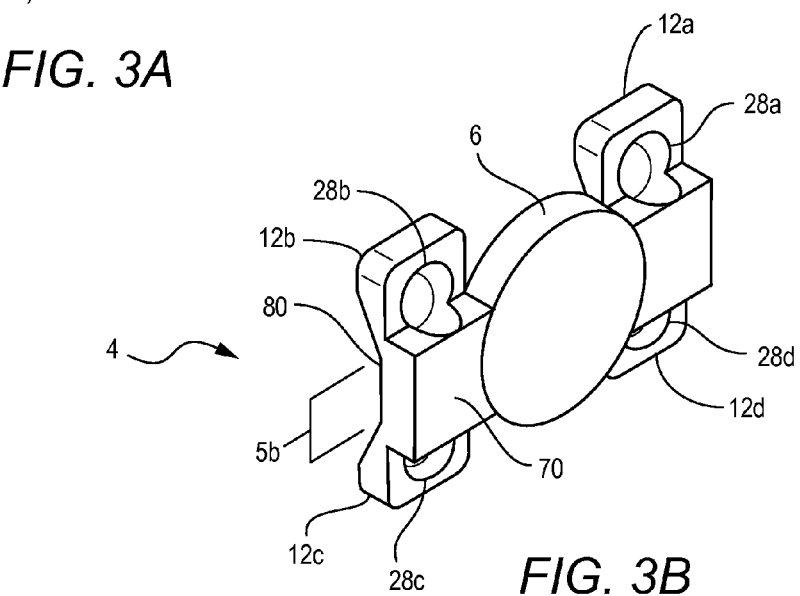
FIG. 3B is a perspective view of the posterior surface of an anterior plate 4.
Figure 5A:
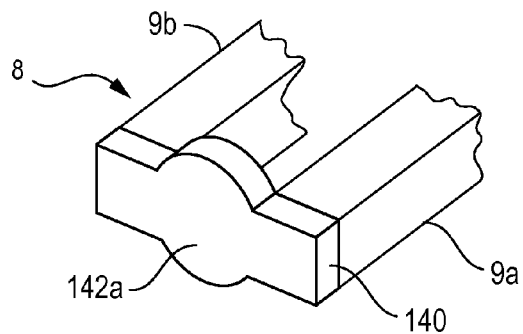
FIGS. 5A-5D are perspective views illustrating four different embodiments of the posterior plate of the spacer.
Figure 5B:
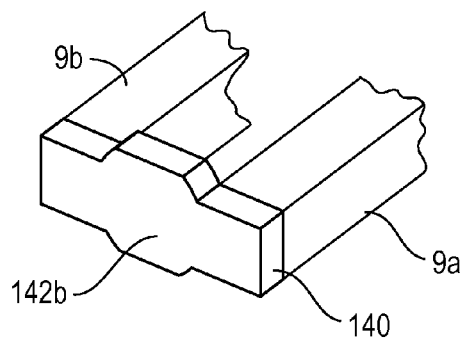
Figure 5C:
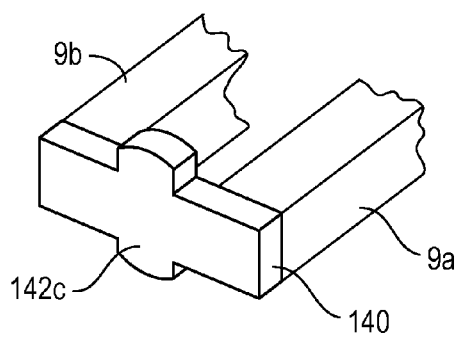
Figure 5D:
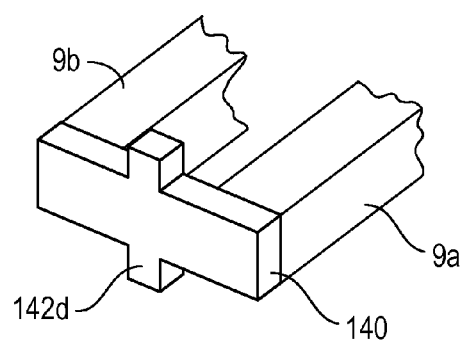

In reference to FIGS. 3A and 3B, the U-shaped spacer 8 further comprises two parallel side walls 9a, 9b, and a posterior wall 140 perpendicular to the side walls 9a, 9b and an open anterior end (see FIGS. 4A-4D, 144). FIG. 3B illustrates a perspective view of the posterior face 70 of the anterior plate 4. When the anterior plate 4 is attached to the spacer 8 during surgery, the plate's posterior face 70 is connected to the spacer's anterior surface 144. FIGS. 3A and 3B also disclose that the two lateral rectangular members 5a,5b of the anterior plate 4 reside aligned on the anterior face 80 and the posterior face 70 with the circular member 6, but that the anchor members 12a-d extend anteriorly from the anterior face 80. As a result, the anterior plate 4 is a low profile or zero profile plate because most of the depth of the circular member 6 and rectangular members 5a,b reside within the intervertebral space 18, while the anchor members 12a-d reside outside of the space 18.

As shown in FIGS. 4A-4D, the side walls 9a,b of the U-shaped spacer 8 further comprise external planar surfaces 146 and two internal concave cylindrically curved surfaces 148 that create a hollow inner chamber 149. In one embodiment, the U-shaped spacer 8 hollow inner chamber 149 is filed with a graft 22 that is cylindrically shaped to tightly contact to the internal curved surfaces 148 (e.g. FIG. 4C) and the endplates 100a,b of the vertebral bodies 24a,b (see FIG. 2A), such that the graft 22 is unable to significantly shift and rotate within the assembly 2.

The graft 22 may comprise a cylindrical bone dowel or milled bone that fits precisely within the cylindrical space that is created by the surgeon within the intervertebral space 18 in order to promote spine fusion between the superior and inferior endplates (FIG. 2A). Graft 22 may further or alternatively comprise bone dust and/or bone substitute and/or aspirated bone marrow. One of skill in the art could readily identify appropriate grafts to insert into the plate-spacer assemblies 2.

In one embodiment, the posterior wall 140 of the spacer 8 is a posterior plate with a planar anterior surface and a planar posterior surface. The posterior plate 140 permanently attaches to the side arms 9a, 9b of the spacer 8 on the anterior surface of plate 140. In another embodiment (not shown), the posterior wall 140 and the side arms 9a, 9b form one U-shaped unit in which the posterior wall 140 is not a separate posterior plate.

Male/Female Connectors: Pertaining to FIGS. 4A-4D, the plate-spacer assemblies 2 of the present invention may further comprise means for securely attaching the anterior plate 4 to the spacer 8. In one embodiment, this may comprise fitting a male member (e.g. FIG. 4A, 182; FIGS. 4B and 4C, 184) extending from the posterior surface 70 of the plate 4 into a female cavity (e.g. FIG. 4A, 183; FIGS. 4B and 4C, 185) on the anterior surface 144 of the spacer 8. The male/female connections may comprise a variety of shapes, including cylindrical (FIG. 4A, 182, 183) or rectangular (FIGS. 4B and 4C, 184, 185), for example. FIG. 4D shows locking members 190 positioned inward from the distal ends of the male members 184 that are configured to fit within the complementary recesses 192 within the female cavity 185. This particular configuration can allow for a more secure fit between the spacer 8 and the anertior plate 4.

Furthermore, the posterior surface 70 of the plate 4 may comprise a cylindrical male member 186 extending posteriorly from the center of the plate 4, wherein it fits within the female cylindrical cavity 187 in the middle of the graft 22.

Four Posterior Plate Embodiments:

As shown in FIGS. 5A-5D, the posterior plate 140 of the U-shaped spacer 8 comprises planar anterior and posterior surfaces with two lateral rectangular members on opposing sides of a middle member. comprising: a circular member (FIG. 5A, 142*a*); a hexagonal member (FIG. 5B, 142*b*); a rectangular member (FIG. 5C, 142*c*); or a cross member (FIG. 5D, 142*d*), or the middle member can be any other suitable shape for the intervertebral implants in accordance with the present invention.

Material Compositions:

Preferred H-shaped anterior plates 4 described herein can be made of any suitable and implantable material including titanium, surgical steel, aluminum, or other metal, polyether ether ketone (PEEK) and, carbon fiber, for example. And preferred U-shaped spacers 8 described herein can be made of any suitable and implantable material including PEEK, carbon fiber, titanium, surgical steel, aluminum, or other metal, natural or synthetic bone, and/or any combination thereof. And preferred grafts 22 described herein can be made of any suitable and implantable material, such as natural or synthetic bone, non-exclusively including bone dowels or milled bone.

Figure 6:
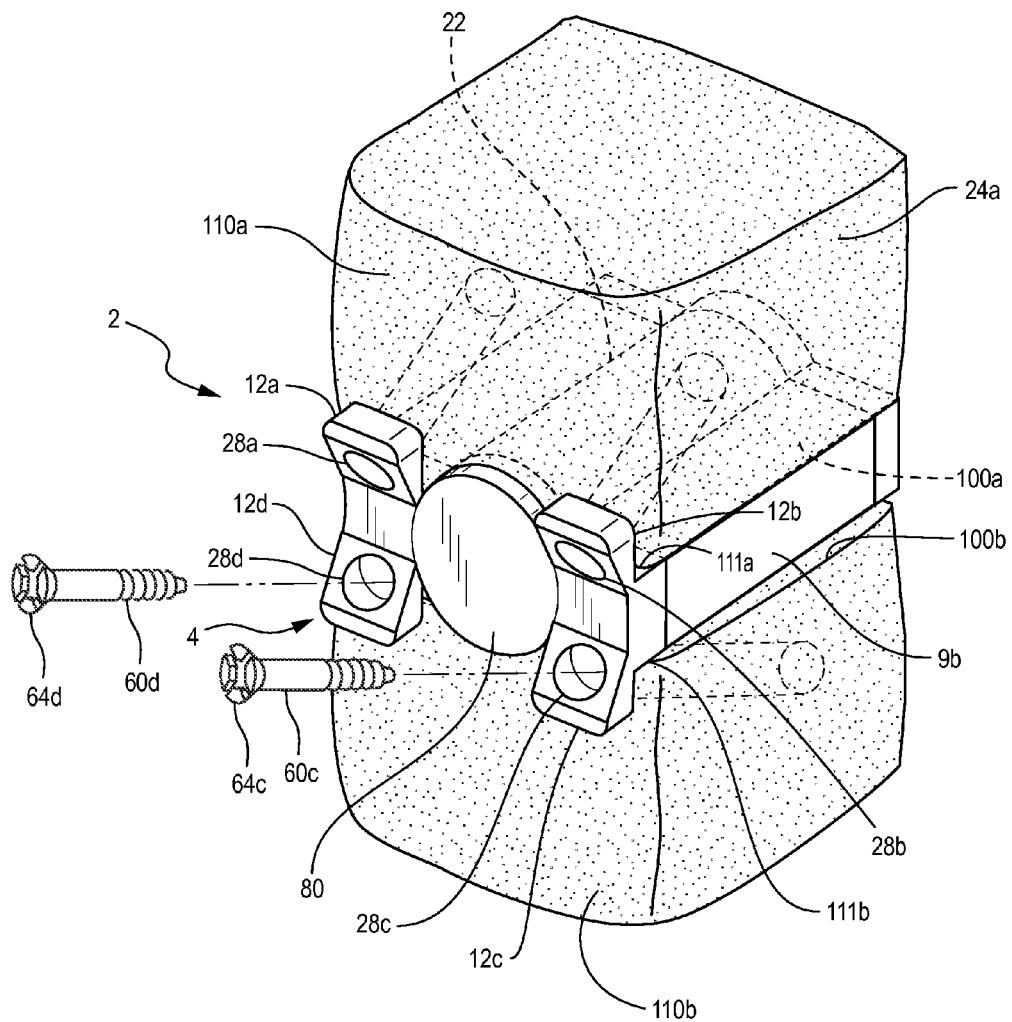
FIG. 6 is a perspective view illustrating a preferred angle of entry of the fastener devices through the anchor members into the vertebral bodies.

Anchor Members:

As shown in FIG. 6, the plate-spacer assemblies 2 provided herein may also include one or more anchor members 12*a-d*. While preferred embodiments are directed to a plate-spacer assembly 2 having four anchor members 12*a-d* protruding at each corner of the anterior face or surface 80 of the anterior plate 4, alternative numbers and positions of anchor members are also contemplated with the embodiments herein. 2, 3, 4, 5, and 6 anchor members, positioned along the anterior face 80 of the plate-spacer assembly 2 whether positioned intermittently, centrally, or in the corners, are readily contemplated herein.

When the plate-spacer assembly 2 is implanted, one or more superior anchor members 12*a* and 12*b* preferably abut against the junction or edge 111*a* of the anterior cortex face 110*a* and the endplate 100*a* of the superior vertebral body 24*a*. Similarly, one or more inferior anchor members 12*c* and 12*d* preferably abut against the junction or edge 111*b* of the anterior cortex face 110*b* and the endplate 100*b* of the inferior vertebral body 24*b*, when the plate-spacer assembly 2 is implanted. Alternatively, 1, 3, or 4 superior anchor elements and 1, 3, or 4 inferior anchor members can be positioned on the plate-spacer assembly.

The vertebral plate-spacer assembly 2 preferably includes means for securely fastening the plate 4 and/or the spacer 8 to the vertebral bodies 24*a* and 24*b*. While the means for securely fastening can be positioned anywhere on the plate-spacer assembly 2, preferred positions are located within the one or more anchor members 12*a-d*. More specifically, the anchor members 12*a-d* can individually include a fastener channel 28*a-d* configured to allow the body of a fastening device 60*a-d*, such as a bone screw, bolt or nail, to pass through and into the bone. Washers, nuts, or other securing means can be used in conjunction with the fastening devices 60*a-d*, to ensure the plate-spacer assembly 2 is securely fastened to the vertebral bodies 24*a* and 24*b*. Preferably the fastener channels 28*a-d* are large enough for only the body of the fastening device 60*a-d*, such as screw bodies, but not the head or cap 64*a-d* of the fastening device (e.g., screw heads) to pass through. The fastener channels 28*a-d* can be sized to fit any desired vertebral fastening device, non-exclusively including screws, bolts, or nails.

According to one embodiment, when the one or more superior anchor members 12*a* and 12*b* are positioned against the anterior cortex face 110*a* of the superior vertebral body 24*a*, their respective fastener channels 28*a* and 28*b* are configured to align with the junction or corner 111*a* created by the intersection of the superior endplate 100*a* and the anterior face 110*a* of the superior vertebral body 24*a*. Likewise, when the one or more inferior anchor members 12*c* and 12*d* are positioned against the anterior cortex face 110*b* of the inferior vertebral body 24*b*, their respective fastener channels 28*c* and 28*d* are configured to align with the junction or corner 111*b*, of the inferior endplate 100*b* and the anterior cortex face 110*b* of the inferior vertebral body 24*b*.

As shown in FIG. 6, the above described alignment of the fastener channels 28*a-d* is advantageous in allowing the bodies 60*a-d* of the fastening devices to be secured within their respective vertebral body 24*a* and 24*b*, through the junction 111*a* and 111*b* of the anterior cortex face 110*a* and 110*b* and its respective endplate 100*a* and 100*b*. Accordingly, the bodies 60*a-d* of the fastening devices are implanted at the same angle through the vertebral junctions 111*a* and 111*b* as the fastener channels 28*a-d* when the plate-spacer assembly 2 is finally positioned within the intervertebral space 18.

The above methods are advantageous because the junction 111*a* and 111*b* of a vertebral body's anterior face 110*a* and 110*b* and its respective endplate 110*a* and 110*b* is hard bone, and allows for stronger fixation by the body 60*a-d* of the fastening device. The bodies of the fastening devices are expressly not implanted perpendicular to the anterior faces 110*a* and 110*b* (in a horizontal, anterior/posterior direction, or transverse plane) or the endplates 100*a* and 100*b* (in a vertical, superior/inferior direction, or a coronal plane) of their targeted vertebral bodies 24*a* and 24*b*. Preferably, the fastening devices, are slightly angled upward when inserted.

Pilot holes (not shown) for the channel members that have a smaller diameter than the bodies 60*a-d* of the fastening devices can be drilled into the vertebral bodies 24*a* and 24*b* prior to or after securing the plate-spacer assembly 2. In one embodiment, the pilot holes are drilled after the plate-spacer assembly is implanted, with the surgeon drilling into and through the channel 28*a-d* of each of the anchor members 12*a-d*. Preferably the pilot holes would be made at the same angles through the junctions 111*a,b* of the anterior faces 110*a,b* and the endplates 100*a,b* as the fastener channels 28*a-d* when the plate assembly 2 is properly positioned within the intervertebral space 18. Alternatively, the bodies of the fastening devices 60*a-d* can be inserted directly into the vertebral bodies 24*a,b* without pilot holes. Templates and other aligning devices can also be used with the teaching herein to align the plate-spacer assemblies 2 and the bodies 60*a,b* and heads 64*a,b* of the fastening devices into their proper positions.

Hinged Plates

Figure 7A:
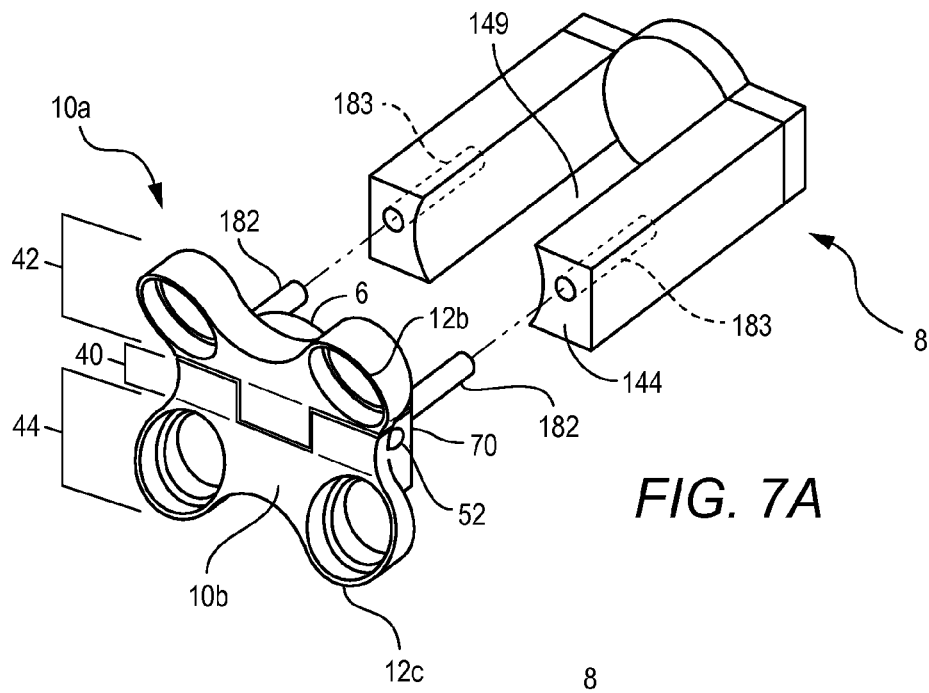
FIGS. 7A-7B illustrate a hinged plate utilized in the plate-spacer assembly of the FIGS. 8A-8B illustrate another embodiment of the plate without anchor members, and with fastener channels located in a circular middle member.
Figure 7B:
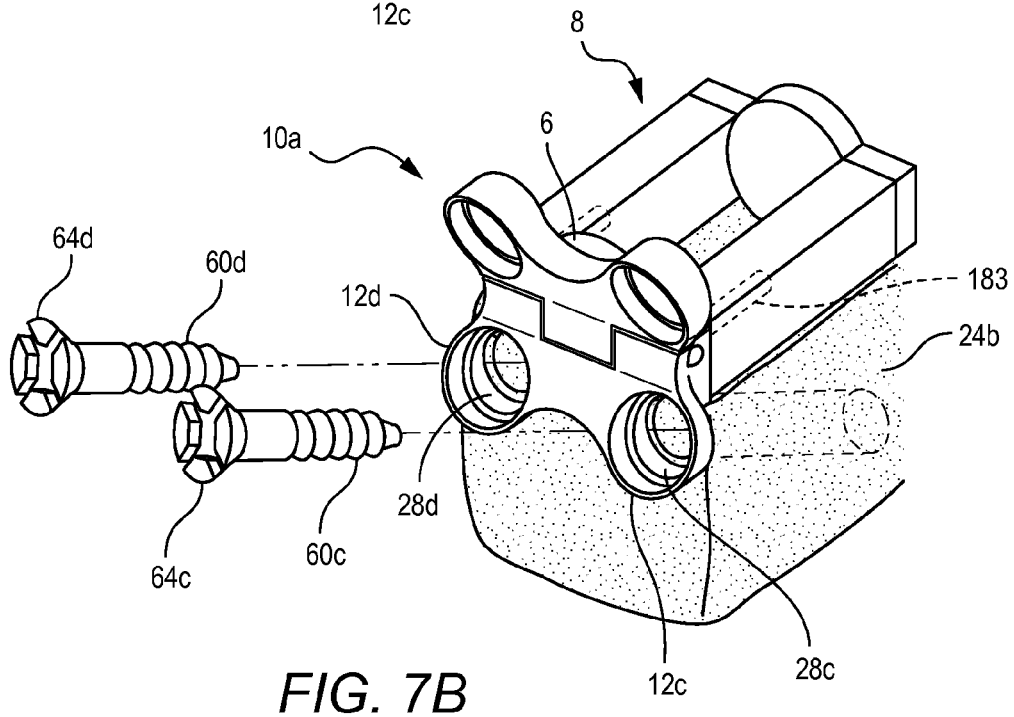

In reference to FIGS. 7A and 7B, the vertebral plate-spacer assembly of the present invention may be used with the hinge anterior plate 10*b* disclosed in U.S. Patent Application 20120065688 by Nehls, and comprising a hinge member 40 to allow the plate assembly 10*b* to flex, or pivot towards the vertebral column at a limited angle or range of motion. The flexing of the hinge member 40 towards the vertebral bodies 24*a* and 24*b* allows the spacer 8 to be under a compressive load, which enhances spinal fusion.

In one embodiment, the anterior plate with the hinge member 10*b* may attach directly onto the anterior surface 144 of the spacer 8. The circular member 6 residing on the posterior surface 70 of the plate fits tightly within the hollow cylindrical cavity 149 on the anterior surface 144 of the spacer 8. In another embodiment (See FIGS. 7A and 7B), the plate-spacer assembly 2 comprising a hinge member 40, may further include female-male connectors, as per FIGS. 4A-4D.

The hinge member 40 traverses laterally along the hinged plate assembly 10b thereby defining a superior plate section 42 and an inferior plate section 44 (as shown in FIGS. 7A and 7B). While in the figures, the superior and inferior plate sections 42 and 44 are different shapes, other suitable shapes (e.g., rectangles, semi-circles, semi-ovals, and the like), including the same shape can also be used with the teachings herein. FIGS. 7A and 7B show the plate assembly 10b in an un-flexed position, where the superior plate section 42 and an inferior plate section 44 define a 180 degree angle, or substantially so.

Hinge members 40 are readily known in the art, and any suitable type of hinge can work with the teachings herein. In general, a hinge member 40 includes a lateral axis of rotation that couples both the superior and anterior sections 42 and 44 of the vertebral plate assembly 10b and allows limited pivotal rotation. Hinge members 40 can advantageously include one or more pivot pins 52, as well knuckles, barrels, springs, prongs, and the like to allow limited flexion towards the vertebral column.

According to preferred teachings, the hinged plate assembly 10b includes means advantageously configured to prevent extension of the superior and inferior plate sections 42 and 44 away from the vertebral body beyond 180 degrees. Additionally, the hinged plate assembly 10b can also include means to prevent excessive pivotal rotation or flexion towards the vertebral bodies 24a and 24b. More specifically, the posterior faces 70a of the superior and inferior plate sections 42 and 44 are configured to allow flexion towards each other at an angle less than 180 degrees (e.g. in FIGS. 7A and 7B, section 42 rotates clockwise, and section 44 rotates counterclockwise). According to even more specific embodiments, the posterior faces of the superior and inferior plate sections 42 and 44 are only permitted very limited flexion towards each other, such that when flexed, the angle degree is about 172 degree, or any of the following ranges: 170-175 degrees, 160-175 degrees, or 171-174 degrees, or substantially so. As those with skill in the art will readily appreciate, these limitations on the angle of pivotal rotation can be done non-exclusively through the use of stops, or other suitable means coupled to the hinged plate assembly 10b.

Advantageously, the hinge member 40 prevents the deformity known as kyphosis, or forward angulation, of the spine and encourages the natural lordotic or inward curvature, of cervical and lumbar regions of the vertebral column. As the spacer 8 is compressed by the superior and inferior vertebral bodies 24a and 24b, the upper and lower plate sections 42 and 44 flex towards each other slightly, thereby preventing kyphosis, and allowing for a preferred degree of lordosis in the vertebral column.

Plate-Spacer Assembly without Anchor Members

Figure 8A:
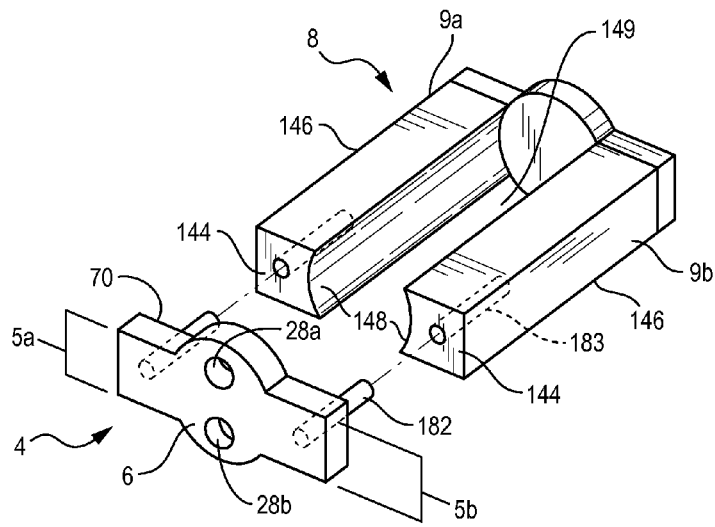
FIG. 8A is an exploded perspective view of one embodiment of the plate-spacer without anchor members and comprising male/female connectors extending from the posterior surface of the plate.
Figure 8B:
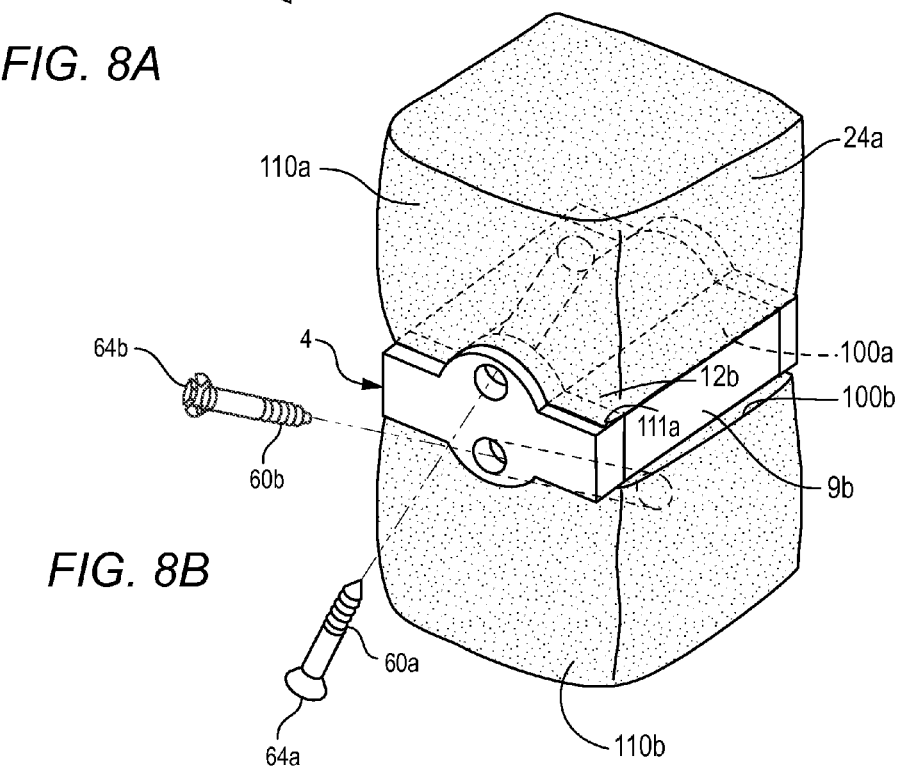
FIG. 8B is a perspective view illustrating a preferred angle of entry of the fastener devices (e.g. screws) through the fastener channels, located in the plate's middle member, and into the vertebral bodies.

In another embodiment, and as illustrated in FIGS. 8A and 8B, the plate-spacer assembly may comprise the same spacer 8 as the previous embodiments, that is affixed to an anterior plate 4 lacking anchor members, the plate comprising: 1) a "middle" (e.g. circular) member 6 residing in the center of the plate; and, 2) two "outer" (e.g. rectangular) members 5a,b extending from the opposing sides of the middle member 6. Again, the middle (e.g. circular) member 6 is size matched to fit the hole created by the surgeon when drilling into the disc during the discectomy; and, to fit the chamber (e.g. cylindrical) 149 on the anterior end of the size matched U-shaped spacer.

It is noted, though, that in this embodiment, the plate 4 is no longer "H-shaped", but is more rectangular with a middle (e.g. circular) center. The plate may comprise one seamless unit, versus three separate members (one middle 6, and two outer members 5a,b) affixed together (see FIG. 8A). The assembly is also partially implanted into the intervertebral space, or it is completely implanted into it so that the anterior face of the plate 4 is essentially aligned with the anterior cortex faces 110a,b of the superior and inferior vertebral bodies (see FIG. 8B).

And in this embodiment as illustrated in FIG. 8B, the anterior plate 4 further comprises fastener channels 28a,b traversing through the thickness of the plate 4, and located within the middle (e.g. circular) member 6 of the plate 4. Bodies 60a,b of the fixation devices are inserted through the channel members 28a,b at an angle to traverse through or near the junctions (e.g. 111a) created by the endplates 100a,b and the superior and inferior anterior cortex faces 110a,b of the vertebral bodies, while the heads or caps 64a,b of the fastening devices are substantially flush or slightly embedded into the anterior face of the plate 4.

The anterior plate 4 may further comprise means for securely attaching the plate 4 to the spacer 8, as shown in FIGS. 4A-4D. In one embodiment, as illustrated in FIG. 8A, this may comprise a male member 182 extending from the posterior face 70 of the plate 4 into a female cavity 183 on the anterior surface 144 of the spacer 8. The male/female connections may comprise a variety of shapes, including cylindrical or rectangular (see FIGS. 4B and 4C, 184, 185), for example.

Method of Implanting the Intervertebral Plate-Spacer Assembly

As shown in FIGS. 2A and 2B, preferably the plate-spacer assemblies 2 described herein are configured to be placed between two vertebral bodies 24a and 24b in the cervical or lumbar region of the spine and thus can be sized accordingly. As the plates assemblies 2 described herein are configured to be fitted partially into an intervertebral space 18, the methods herein are exclusively directed to anterior implantation within the vertebral column. Assemblies and methods directed to posterior vertebral implantation are expressly excluded herein.

In accordance with one ADCF implantation surgical procedure, a surgeon first makes an incision on the anterior surface of the patient's neck, and removes the afflicted intervertebral disc (discectomy) and/or one or more vertebral bodies (corpectomy), or portions thereof. Distractors and methods of discectomy and corpectomy are known in the art and any suitable one can be used with the teachings herein. One non-exclusive example of a distractor/retractor that can be used for separating vertebral bodies is disclosed in U.S. Pat. No. 7,494,463 to Daniel G. Nehls, which is hereby expressly incorporated by reference herein in its entirety.

Figure 9A:
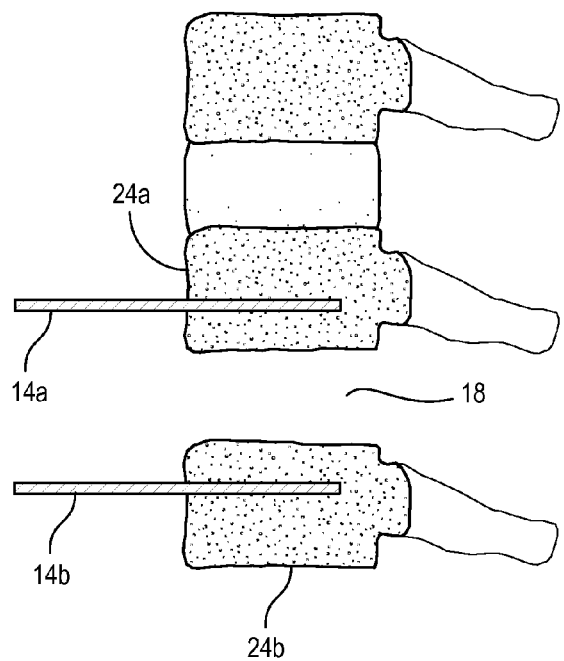
FIGS. 9A-9J illustrate methods of surgically implanting the plate-spacer assemblies of the present invention.
Figure 9B:
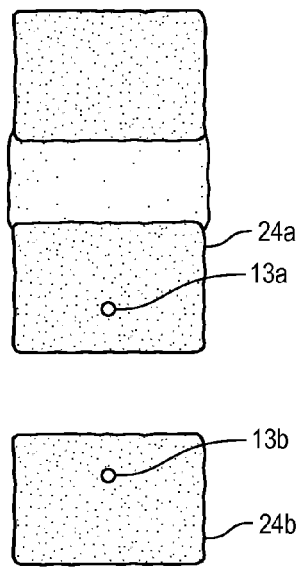

As illustrated in FIG. 9A, distractor pins 14a and 14b are individually fixed perpendicularly to vertebral bodies 24a and 24b respectively, which are positioned superior and inferior to the designated disc or section being removed, thus creating an intervertebral space 18. Typically, the distractor pins 14a and 14b are screwed into the vertebral bodies 24a and 24b via holes 13a and 13b that are drilled into the bodies, as shown in FIG. 9B.

A distractor tool (not shown) may also be used to engage the exposed heads of the pins 14*a* and 14*b* and expand them to mechanically separate the vertebral bodies 24*a* and 24*b* so as to allow the surgeon better access to the designated disc or intervertebral section to be removed.

Figure 9C:
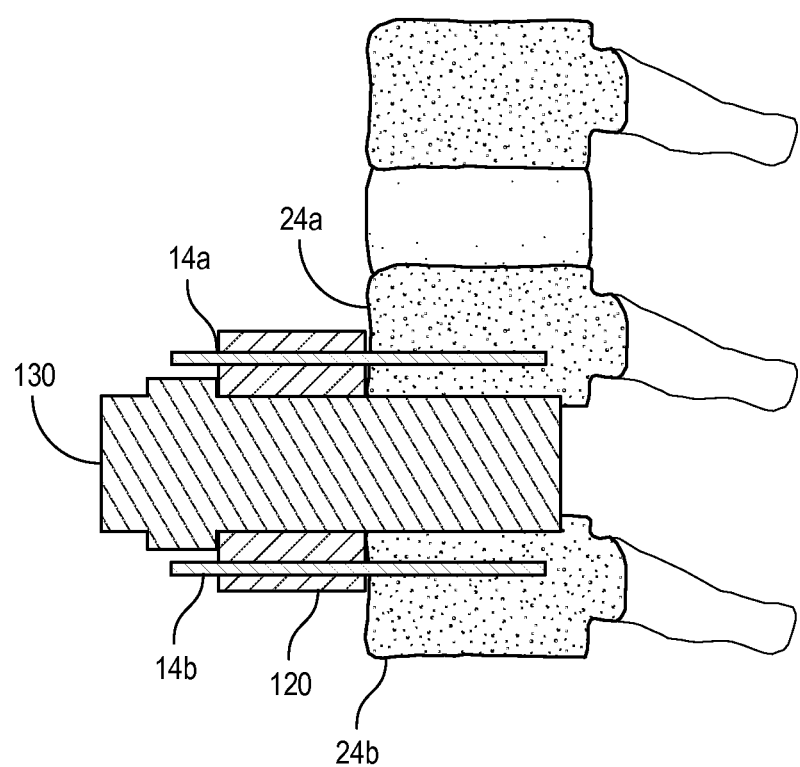
Figures 9D, 9E:
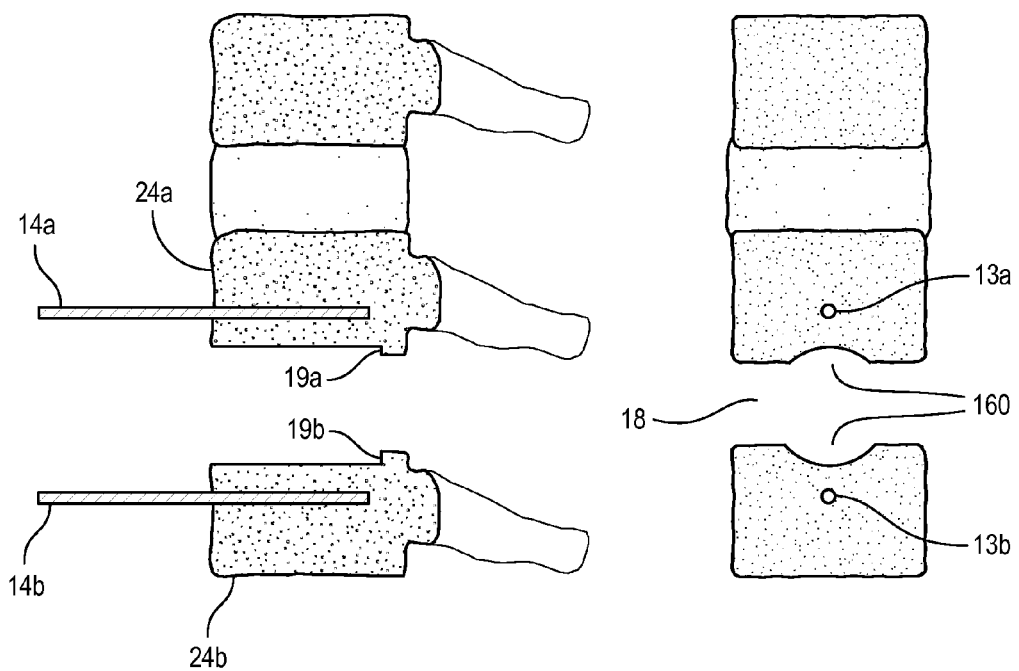

As illustrated in the cross-sectional view of FIGS. 9C and 9D, the surgeon next inserts the milling guide 120, followed by a reamer 130 being inserted into the milling guide 120. The reamer/milling guide are also used to create a cylindrically shaped channel 160 within the intervertebral space 18 for a cylindrical graft (e.g. bone dowel) within the spacer 8 to fit snugly into (FIG. 9E). In one embodiment, a handheld mill can create a horizontal cylindrical bore in the middle of the intervertebral space 18. Preferably the bore does not traverse the entire anterior/posterior distance of the vertebral bodies 24*a* and 24*b* such that upper and lower shelves 19*a* and 19*b* are created on the endplates 100*a* and 100*b*. These shelves 19*a* and 19*b* are advantageous in preventing the spacer 8 and graft 22 from inadvertently dislodging posteriorly into the spinal canal by placing a stop behind the spacer's posterior wall 140 (see FIGS. 9F and 9G).

Figure 9F:
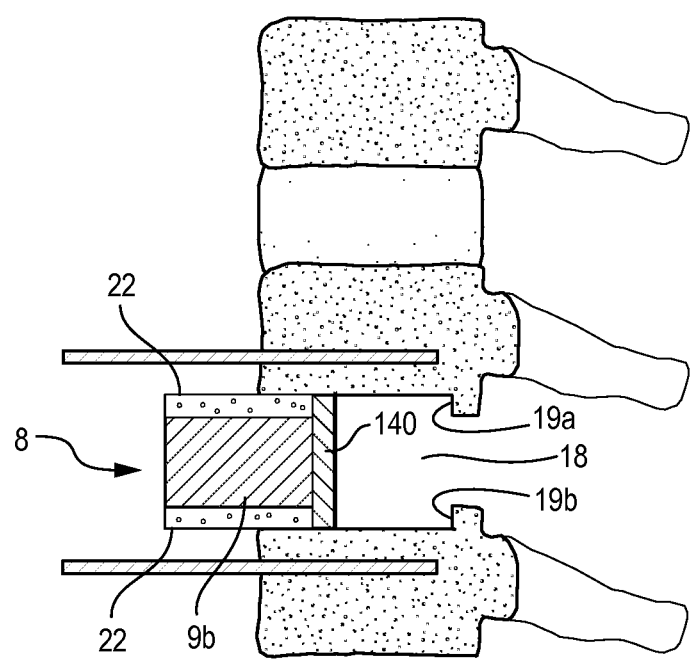

After the designated disc material and/or vertebral body are removed, a graft 22 (e.g. cylindrical bone dowel) within the U shaped spacer 8 can be inserted into the resulting space, using techniques and materials that are well known in the art (FIG. 9F). In another embodiment, the U shaped spacer 8 is inserted into the intervertebral space 18 first, followed by the cylindrical graft 22 being inserted into the spacer 8.

Figure 9G:
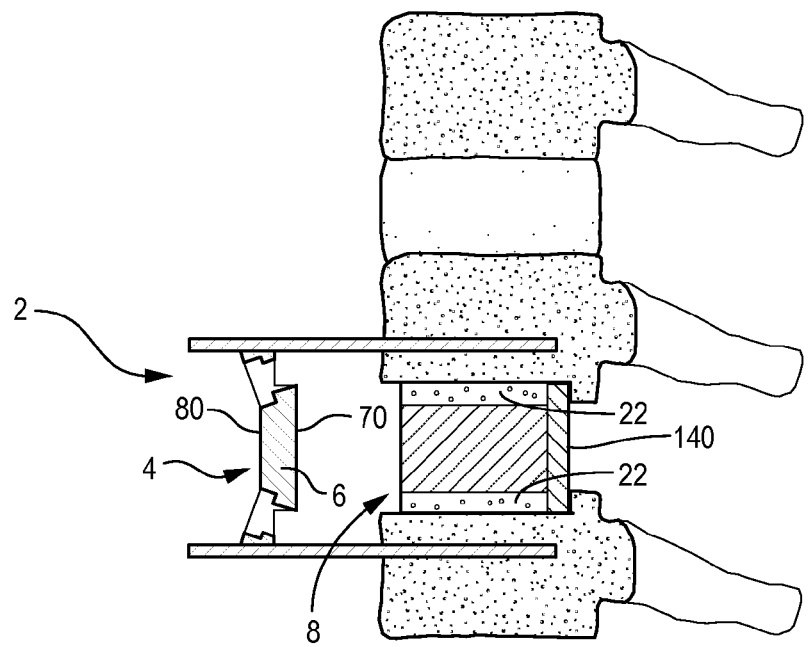

The H shaped anterior plate 4 is then placed over the anterior end of the spacer 8. The posterior surface 70 of the anterior plate's circular member 6 fits into the cylindrical shaped anterior end of the spacer 8 to create a tight seal (FIG. 9G). This seal prevents the seepage of any material within the spacer (e.g. bone dust) and/or the rotation and shifting of a graft 22 within the spacer, thus promoting stability and spinal fusion.

Figure 9H:
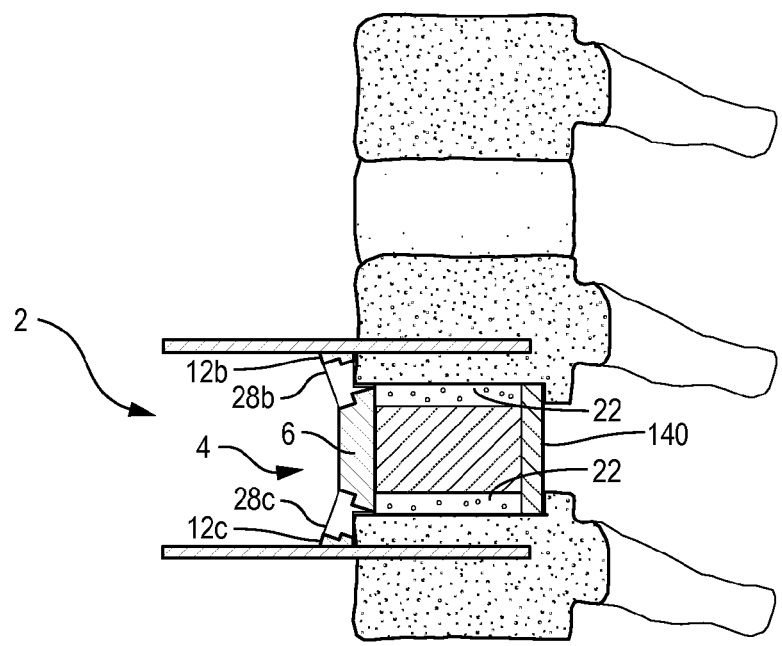

Low Profile Plate:

According to one embodiment, the size of the plate-spacer assembly 2 is low profile such that it is configured with the entire U shaped spacer 8 implanted within the intervertebral space 18, while only a portion of the H shaped anterior plate 4 is implanted within the intervertebral space 18 and a portion of the plate assembly 4 is implanted anteriorly to the intervertebral space 18. More specifically, a surgeon can implant the posterior face 70 of the plate 4 into the intervertebral space 18, but not the anterior face 80 of the plate 4, as shown in FIGS. 9G and 9H. In another embodiment, the anterior face 80 is aligned with the anterior cortex of the superior and inferior vertebral bodies such that only the anchor members (12*b*, 12*d*) of the H shaped anterior plate 4 extend anteriorly from the intervertebral space 18 (not shown).

Lastly, the surgeon drills pilot holes through channel members (see FIG. 6, 28*a-d*) and affixes fastening devices 60*a-d* with bodies (e.g. four screws) (see FIG. 9I, 64*b*, 64*d*) to secure the vertebral plate-spacer assembly 2 to the superior and inferior vertebral bodies 24*a,b*. In one embodiment, the pilot holes traverse through the junctions or corners created by the anterior cortex faces contacting the vertebral endplates of the superior and inferior vertebral bodies.

Pilot holes for channels 28*a-d* having a smaller diameter than the bodies of the fastening devices 60*a-d* can be drilled into the vertebral bodies 24*a* and 24*b* prior to or after securing the plate-spacer assembly 2. Preferably the pilot holes would be made at the same angles through the junctions 111*a* and 111*b* of the anterior faces 110*a* and 110*b* and the endplates 100*a* and 100*b* as the fastener channels 28*a-d* when the plate-spacer assembly 2 is properly positioned within the intervertebral space 18. Alternatively, the bodies of the fastening devices 60*a-d* can be inserted directly into the vertebral bodies 24*a* and 24*b* without pilot holes. Templates and other aligning devices can also be used with the teaching herein to align the plate-spacer assembly 2 and the fastening devices 60*a-d* into their proper positions.

After the fastening devices 60*a-d* are securely in position within the superior and inferior vertebral bodies 24*a,b*, then the distractor pins 14*a* and 14*b* are compressed together to tighten the bond between the spacer 8 and graft 22, and the endplates 100*a,b* to promote stability and spinal fusion. The distractor pins 14*a,b* are then removed and the surgical incision is closed.

Anterior Plate without Anchor Members

Figure 9I:
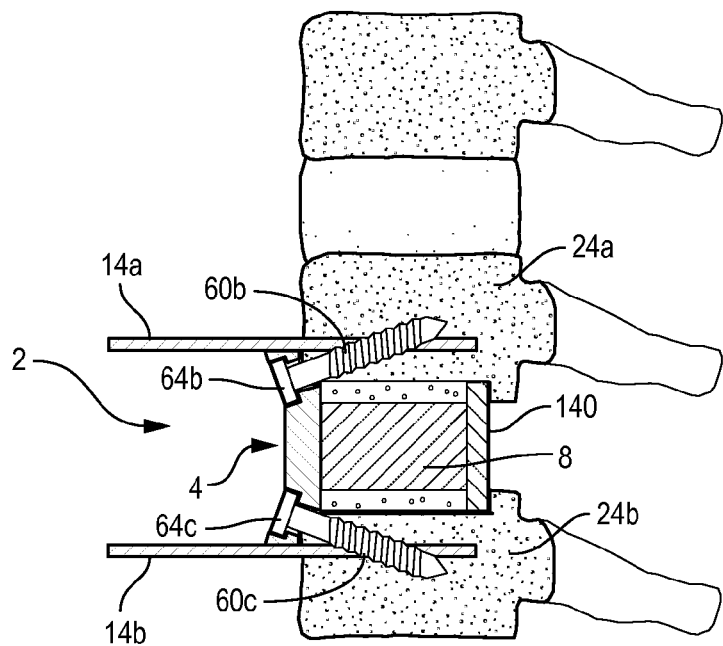
Figure 9J:
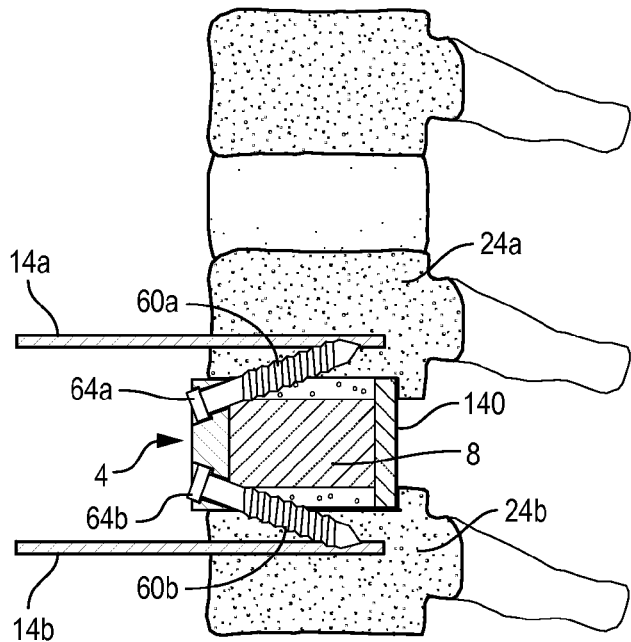

In another embodiment of the anterior plate as illustrated in FIG. 9J, the anchor members 12*a-d* are absent from the four corners of the anterior plate 4. Instead, two or more fastener channels are located within the middle (e.g. circular) member 6.

The method of implantation for this embodiment is illustrated in FIG. 9I, and is nearly the same as per the implantation and fixation of the H-shaped plate, as per FIGS. 9A-9I, with the exception of the location of the pilot holes for the fastener channels 28*a,b*. Two pilot holes for channels 28*a,b* are drilled into the vertebral bodies 24*a* and 24*b* prior to or after securing the plate-spacer assembly 2. Preferably the pilot holes would be made at the same angles through the junctions 111*a* and 111*b* of the anterior faces 110*a* and 110*b* and the endplates 100*a* and 100*b* as the fastener channels 28*a-d* when the plate-spacer assembly 2 is properly positioned within the intervertebral space. Alternatively, the bodies of the fastening devices 60*a,b* can be inserted directly into the vertebral bodies 24*a* and 24*b* without pilot holes. Templates and other aligning devices can also be used with the teaching herein to align the plate-spacer assembly 2 and the bodies of the fastening devices 60*a,b* into their proper positions. The fastening devices are then inserted at an angle through the channels near or at the junctions 111*a,b* of the vertebral bodies 24*a,b* until the fastening device's body 60*a,b* is affixed into the cortical bone of the vertebral bodies 24*a,b* (see FIG. 9J). The wider heads 64*a,b* of the fastening devices are secured within the channels and flush with the anterior surface/face of the plate 4. According to non-preferred embodiments, those with skill in the art will recognize the assemblies herein comprising both a separate spacer and separate anterior plate can be made with the anterior plate permanently attached to the anterior end of the spacer, thereby creating a single piece. According to these embodiments, the spacer has a closed anterior face which comprises an anterior plate. The graft, insert, bone dowel, bone dust, demineralized bone matrix, bone paste, etc. can be inserted into these singular pieces from above, then can be fully inserted into the intervertebral space.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description. It is particularly noted, that although the various embodiments have been described in reference to a specific procedure (i.e. Anterior Cervical Discectomy and Fusion (ACDF)), the plate-spacer assemblies disclosed herein may be used in an anterior spinal fusion procedure for any part of the spine (e.g. lumbar, thoracic, sacral, and cervical).

What is claimed is:

1. A method of implanting a vertebral plate and spacer assembly within an intervertebral space between superior and inferior vertebral bodies each having anterior cortex faces and vertebral endplates, comprising:
   a) providing a U-shaped spacer having two parallel side walls with an internal curved surface, external surfaces, a posterior wall perpendicular to and connecting the side walls, and an open anterior end;
   b) providing a vertebral plate having
      (i) a middle member in a center of the plate with a posterior surface and an anterior surface;
      ii) first and second outer members each with a posterior and anterior surface and extending laterally from two opposing sides of the middle member, wherein the posterior surfaces of the first and second outer members are configured to tightly fit within the intervertebral space;
      iii) channels individually traversing through the vertebral plate and adapted to receive fastening devices for securely fixing the vertebral plate to the superior and inferior vertebral bodies at junctions created by the anterior cortex faces and the vertebral endplates, and into cortical bone of the vertebral bodies;
   c) following a discectomy,
      i) creating a substantially rectangular space posteriorly from the anterior end of an intervertebral space;
      ii) drilling a hole extending posteriorly from the anterior end of the intervertebral space and centered within the rectangular space, wherein the hole creates a shelf on both the superior and inferior endplates of the vertebral bodies;
   d) after drilling the hole, inserting the U-shaped spacer into the rectangular space and hole such that posterior wall of the spacer abuts against the shelf on the superior and inferior endplates to prevent posterior dislodgement of the spacer, and the open anterior end faces the anterior end of the intervertebral space;
   e) affixing the vertebral plate by inserting the middle member tightly into the hole while concurrently inserting the posterior surface of the outer members into the rectangular space until the anterior surface of the plate is substantially aligned with, or slightly protruding from, the anterior end of the intervertebral space, while the channels abut against the anterior cortex faces; and,
   f) inserting fastening devices, through the channels and into the superior and inferior vertebral bodies at the junctions and into cortical bone of the vertebral bodies.

2. The method of claim 1, wherein the spacer is hollow and lacks a superior and inferior wall, and spine fusion occurs between the endplates of the superior and inferior vertebral bodies and within the spacer.

3. The method of claim 1, further comprising positioning an insert within the spacer that tightly contacts the internal surfaces of the spacer's side walls and posterior wall and the posterior surface of the middle member of the plate, such that the insert is unable to shift and rotate within the spacer.

4. The method claim 1, wherein the hole in the rectangular space is created by a guided reamer that is removed after the hole is created.

5. The method of claim 1, further comprising joining the vertebral plate to the spacer with -male-female connectors, wherein each male connector extends posteriorly from the first and second outer members of the vertebral plate and fits into a complementary female connector on the anterior surface of the spacer side walls.

6. The method of claim 1, wherein the external surfaces of the assembly are planar, the middle member of the plate is circular or oval, and the outer members of the plate are rectangular or square.

7. The method of claim 1, wherein the plate further comprises a hinge member that laterally traverses across it, thereby defining a superior and inferior sections with limited flexion towards the superior and inferior vertebral bodies when implanted.

8. The method of claim 1, wherein the plate is H-shaped and a plurality of anchor members are coupled to the outer members, such that the anchor members are configured to affix to the junction created by the anterior cortex faces and the intervertebral endplates, and the channels traverse through the anchor members.

9. The method of claim 1, wherein the channels traverse through the middle member of the vertebral plate.

10. A method of implanting a vertebral plate and spacer assembly within an intervertebral space between superior and inferior vertebral bodies each having anterior cortex faces and vertebral endplates, comprising:
    a) providing a U-shaped spacer having two parallel side walls with an internal curved surface, external surfaces, a posterior wall perpendicular to and connecting the side walls, and an open anterior end;
    b) providing a vertebral plate having
       (i) a middle member in a center of the plate with a posterior surface and an anterior surface;
       ii) first and second outer members each with a posterior and anterior surface and extending laterally from two opposing sides of the middle member, wherein the posterior surfaces of the first and second outer members are configured to tightly fit within the intervertebral space;
       iii) channels individually traversing through the vertebral plate and adapted to receive fastening devices for securely fixing the vertebral plate to the superior and inferior vertebral bodies, and into cortical bone of the vertebral bodies;
    c) following a discectomy,
       i) creating a substantially rectangular space posteriorly from the anterior end of an intervertebral space;
       ii) drilling a hole extending posteriorly from the anterior end of the intervertebral space and centered within the rectangular space wherein the hole creates a shelf on both the superior and inferior endplates of the vertebral bodies;
    d) after drilling the hole, inserting the U-shaped spacer into the rectangular space and hole such that posterior wall of the spacer abuts against the shelf on the superior and inferior endplates to prevent posterior dislodgement of the spacer, and the open anterior end faces the anterior end of the intervertebral space;
    e) affixing the vertebral plate by inserting the middle member tightly into the hole while concurrently inserting the posterior surface of the outer members into the rectangular space until the anterior surface of the plate is substantially aligned with, or slightly protruding from, the anterior end of the intervertebral space, while the channels abut against the anterior cortex faces; and,
    f) inserting fastening devices through the channels and into the superior and inferior vertebral bodies.

11. The method of claim 10, wherein the spacer is hollow and lacks a superior and inferior wall, and spine fusion occurs between the endplates of the superior and inferior vertebral bodies and within the spacer.

12. The method of claim 10, further comprising positioning an insert within the spacer that tightly contacts the internal surfaces of the spacer's side walls and posterior wall and the posterior surface of the middle member of the plate, such that the insert is unable to shift and rotate within the spacer.

13. The method claim 10, wherein the hole in the rectangular space is created by a guided reamer that is removed after the hole is created.

14. The method of claim 10, further comprising joining the vertebral plate to the spacer with male-female connectors, wherein each male connector extends posteriorly from the laterally opposing ends of the vertebral plate and fits into a complementary female connector on the anterior surface of the spacer side walls.

15. The method of claim 10, wherein the external surfaces of the assembly are planar, the middle member of the plate is circular or oval, and the outer members of the plate are rectangular or square.

16. The method of claim 10, wherein the plate further comprises a hinge member that laterally traverses across it, thereby defining a superior and inferior sections with limited flexion towards the superior and inferior vertebral bodies when implanted.

17. The method of claim 10, wherein the plate is H-shaped and a plurality of anchor members are coupled to the outer members, such that the anchor members are configured to affix to the junction created by the anterior cortex faces and the intervertebral endplates, and the channels traverse through the anchor members.

18. The method of claim 10, wherein the channels traverse through the middle member of the vertebral plate.

* * * * *